US00PP22849P2

(12) United States Plant Patent
Kanaya et al.

(10) Patent No.: US PP22,849 P2
(45) Date of Patent: Jul. 10, 2012

(54) ***VERBENA* PLANT NAMED 'SUNMARICOAKA'**

(50) Latin Name: *Verbena hybrida*
Varietal Denomination: Sunmaricoaka

(75) Inventors: Takeshi Kanaya, Shiga (JP); Tomoya Misato, Yamanashi (JP)

(73) Assignee: Suntory Flowers Ltd., Tokyo (JP)

( * ) Notice: Subject to any disclaimer, the term of this patent is extended or adjusted under 35 U.S.C. 154(b) by 314 days.

(21) Appl. No.: 12/658,044

(22) Filed: Feb. 1, 2010

(51) Int. Cl.
*A01H 5/00* (2006.01)

(52) U.S. Cl. ..... Plt./308

(58) Field of Classification Search ..... Plt./308
See application file for complete search history.

(56) References Cited

U.S. PATENT DOCUMENTS

PP10,311 P * 3/1998 Tachibana ..... Plt./308

OTHER PUBLICATIONS

UPOV ROM GTITM Computer Database, GTI Jouve Retrieval Software 2011/10 Citation for 'Sunmaricoaka'.*

* cited by examiner

*Primary Examiner* — Wendy C Haas
(74) *Attorney, Agent, or Firm* — C. A. Whealy

(57) ABSTRACT

A new and distinct cultivar of *Verbena* plant named 'Sunmaricoaka', characterized by its compact and mounding to cascading plant habit; vigorous growth habit; freely branching habit; early and freely flowering habit; long flowering period; red-colored flowers that are held above and beyond the foliar plane; and good garden performance.

1 Drawing Sheet

Botanical designation: *Verbena hybrida.*
Cultivar denomination: 'SUNMARICOAKA'.

REFERENCED TO CLOSELY-RELATED APPLICATIONS

Title: *Verbena* Plant Named 'Sunmaricomu'.
Applicants: Takeshi Kanaya & Tomoya Misato.
(U.S. Plant patent application Ser. No. 12/658,043).

BACKGROUND OF THE INVENTION

The present invention relates to a new and distinct cultivar of *Verbena* plant, botanically known as *Verbena hybrida*, and hereinafter referred to by the name 'Sumnaricoaka'.

The new *Verbena* plant is a product of a planned breeding program conducted by the Inventors in Higashiomi, Shiga, Japan. The objective of the breeding program is to create new compact, mounding and freely-branching *Verbena* cultivars with attractive flower coloration.

The new *Verbena* plant originated from a cross-pollination made by the Inventors in November, 2005 in Higashiomi, Shiga, Japan of a proprietary selection of *Verbena hybrida* identified as code number 00-17, not patented, as the female, or seed, parent with a proprietary selection of *Verbena hybrida* identified as code number 00-20, not patented, as the male, or pollen, parent. The new *Verbena* plant was discovered and selected by the Inventor as a single flowering plant within the progeny of the stated cross-pollination in a controlled greenhouse environment in Higashiomi, Shiga, Japan in October, 2006.

Asexual reproduction of the new *Verbena* plant by terminal cuttings in a controlled environment in Higashiomi, Shiga, Japan since November, 2006 has shown that the unique features of this new *Verbena* plant are stable and reproduced true to type in successive generations.

SUMMARY OF THE INVENTION

Plants of the new *Verbena* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunmaricoaka'. These characteristics in combination distinguish 'Sunmaricoaka' as a new and distinct cultivar of *Verbena:*

1. Compact and mounding to cascading plant habit.
2. Vigorous growth habit.
3. Freely branching habit.
4. Early and freely flowering habit.
5. Long flowering period.
6. Red-colored flowers that are held above and beyond the foliar plane.
7. Good garden performance.

Plants of the new *Verbena* can be compared to plants of the female parent selection. Plants of the new *Verbena* differ primarily from plants of the female parent selection in the following characteristics:

1. Plants of the new *Verbena* are more compact than plants of the female parent selection.
2. Plants of the new *Verbena* are not as upright as plants of the female parent selection.
3. Plants of the new *Verbena* and the female parent selection differ in flower color as plants of the female parent selection have violet-colored flowers.

Plants of the new *Verbena* can be compared to plants of the male parent selection. Plants of the new *Verbena* differ primarily from plants of the male parent selection in the following characteristics:

1. Plants of the new *Verbena* are more compact than plants of the male parent selection.
2. Plants of the new *Verbena* are not as upright as plants of the male parent selection.
3. Plants of the new *Verbena* and the male parent selection differ in flower color as plants of the male parent selection have lavender-colored flowers.

Plants of the new *Verbena* can be compared to plants of *Verbena* 'Sunmaricomu', disclosed in U.S. Plant patent application Ser. No. 12/658,043. Plants of the new *Verbena* differ primarily from plants of 'Sunmaricomu' in flower color as plants of 'Sunmaricomu' have red purple-colored flowers.

Plants of the new *Verbena* can be compared to plants of *Verbena* 'Sunvp-su', disclosed in U.S. Plant Pat. No. 10,311. In side-by-side comparisons conducted in Higashiomi, Shiga, Japan, plants of the new *Verbena* differed primarily from plants of 'Sunvp-su' in the following characteristics:

1. Plants of the new *Verbena* were more compact than plants of 'Sunvp-su'.
2. Plants of the new *Verbena* were not as trailing as plants of 'Sunvp-su'.
3. Plants of the new *Verbena* flowered earlier than plants of 'Sunvp-su'.
4. Plants of the new *Verbena* had larger inflorescences and flowers than plants of 'Sunvp-su'.
5. Flowers of plants of the new *Verbena* had broader petals than flowers of plants of 'Sunvp-su'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena*.

The photograph at the top of the sheet comprises a side perspective view of a typical flowering plant of 'Sunmaricoaka' grown in a container.

The photograph at the bottom of the sheet is a close-up view of a typical inflorescence of 'Sunmaricoaka'.

DETAILED BOTANICAL DESCRIPTION

The aforementioned photographs and following observations and measurements describe plants grown in 15-cm containers in Higashiomi, Shiga, Japan, under commercial practice during the spring and early summer in an outdoor nursery with day temperatures averaging 23° C. and night temperatures averaging 13° C. Plants were four months old when the photographs and description were taken. In the following description color references are made to The Royal Horticultural Society Colour Chart, 2001 Edition, except where general terms of ordinary dictionary significance are used.

Botanical classification: *Verbena hybrida* 'Sunmaricoaka'.

Parentage:

*Female, or seed, parent*.—Proprietary selection of *Verbena hybrida* identified as code number 00-17, not patented.

*Male, or pollen, parent*.—Proprietary seedling selection of *Verbena hybrida* identified as code number 00-20, not patented.

Propagation:

*Type*.—By terminal cuttings.

*Time to initiate roots*.—About 10 to 14 days at 20° C. to 25° C.

*Time to produce a rooted young plant*.—About four weeks at 20° C. to 25° C.

*Root description*.—Fibrous; white in color.

*Rooting habit*.—Freely branching.

Plant description:

*Plant and growth habit*.—Compact, initially upright to mounding to cascading growth habit; freely branching habit with numerous lateral branches developing per plant; pinching enhances lateral branch development; vigorous growth habit.

*Plant height*.—About 21 cm.

*Plant diameter*.—About 40.8 cm.

Lateral branch description:

*Length*.—About 18.4 cm.

*Diameter*.—About 2.4 mm.

*Internode length*.—About 3.4 cm.

*Strength*.—Strong.

*Aspect*.—Upright to decumbent.

*Texture*.—Pubescent.

*Color*.—Close to 144A.

Foliage description:

*Arrangement*.—Opposite, simple.

*Length*.—About 4.7 cm.

*Width*.—About 2.7 cm.

*Shape*.—Narrowly ovate.

*Apex*.—Acute.

*Base*.—Truncate to obtuse.

*Margin*.—Serrate.

*Texture, upper and lower surfaces*.—Coarse; pubescent.

*Venation pattern*.—Pinnate; reticulate.

*Color*.—Developing leaves, upper surface: Close to 137B. Developing leaves, lower surface: Close to 147B. Fully expanded leaves, upper surface: Close to 137A; venation, close to 145C. Fully expanded leaves, lower surface: Close to 147B; venation, close to 145C.

*Petiole*.—Length: About 5.5 cm. Diameter: About 2.4 mm. Texture, upper and lower surfaces: Sparsely pubescent. Color, upper and lower surfaces: Close to 145C.

Flower description:

*Flower arrangement and habit*.—Single salverform flowers arranged in hemispherical terminal racemes; flowers face mostly upright; freely flowering habit with about 28 flowers per inflorescence and about 13 inflorescences per plant.

*Natural flowering season*.—Early flowering habit, plants begin flowering about four weeks after planting; long flowering period, plants flower continuously from spring to late autumn in Japan.

*Flower longevity*.—Flowers last about one week on the plant; flowers not persistent.

*Fragrance*.—None detected.

*Inflorescence height*.—About 5.6 cm.

*Inflorescence diameter*.—About 6.7 cm.

*Flowers*.—Appearance: Flared trumpet, corolla fused, five-parted. Diameter: About 2.6 cm. Depth (height): About 2.6 cm. Tube length: About 2 cm. Tube diameter: About 1.8 mm.

*Flower buds*.—Length: About 1.6 cm. Diameter: About 3.8 mm. Shape: Clavate. Color: Close to 53B.

*Corolla*.—Arrangement: Single whorl of five fused petals. Petal length: About 10.8 mm. Petal width: About 11.7 mm. Petal lobe shape: Obcordate. Petal lobe apex: Cordate. Petal margin: Entire; slightly undulate.

Petal texture, upper and lower surfaces: Smooth, glabrous. Tube texture: Smooth, glabrous. Color: Petal, when opening and fully opened, upper surface: Close to 45B; towards the base, close to 46A; center, close to 157D. Petal, when opening and fully opened, lower surface: Close to 65C. Throat: Close to 145D. Tube: Close to 145D.

*Calyx*.—Arrangement: One single narrow calyx tube per flower with five fused sepals. Sepal length: About 12.1 mm. Sepal width: About 1 mm. Sepal shape: Lanceolate. Sepal apex: Acute. Sepal margin: Entire. Sepal texture, upper and lower surfaces: Smooth, glabrous. Sepal color, upper and lower surfaces: Close to 137C.

*Peduncles*.—Length: About 6.4 cm. Diameter: About 1.9 mm. Strength: Strong. Texture: Pubescent. Color: Close to 144A.

*Reproductive organs*.—Stamens: Quantity/arrangement: Four per flower, adnate to corolla tube. Stamen length: About 2 cm. Anther shape: Ellipsoidal. Anther size: About 0.7 mm by 0.4 mm. Anther color: Close to 154B. Pollen amount: Scarce. Pollen color: Close to 154D. Pistils: Quantity: One per flower. Pistil length: About 18.7 mm. Stigma shape: Bi-parted. Stigma color: Close to 144B. Style color: Close to 145C. Ovary color: Close to 144A. Fruits/seeds: Fruit and seed development have not been observed.

Garden performance: Plants of the new *Verbena* have been observed to have good garden performance and to tolerate wind, rain and temperatures from about 0° C. to about 35° C.

Pathogen/pest resistance: Plants of the new *Verbena* have not been observed to be resistant to pathogens and pests common to *Verbenas*.

It is claimed:

1. A new and distinct *Verbena* plant named 'Sunmaricoaka' as illustrated and described.

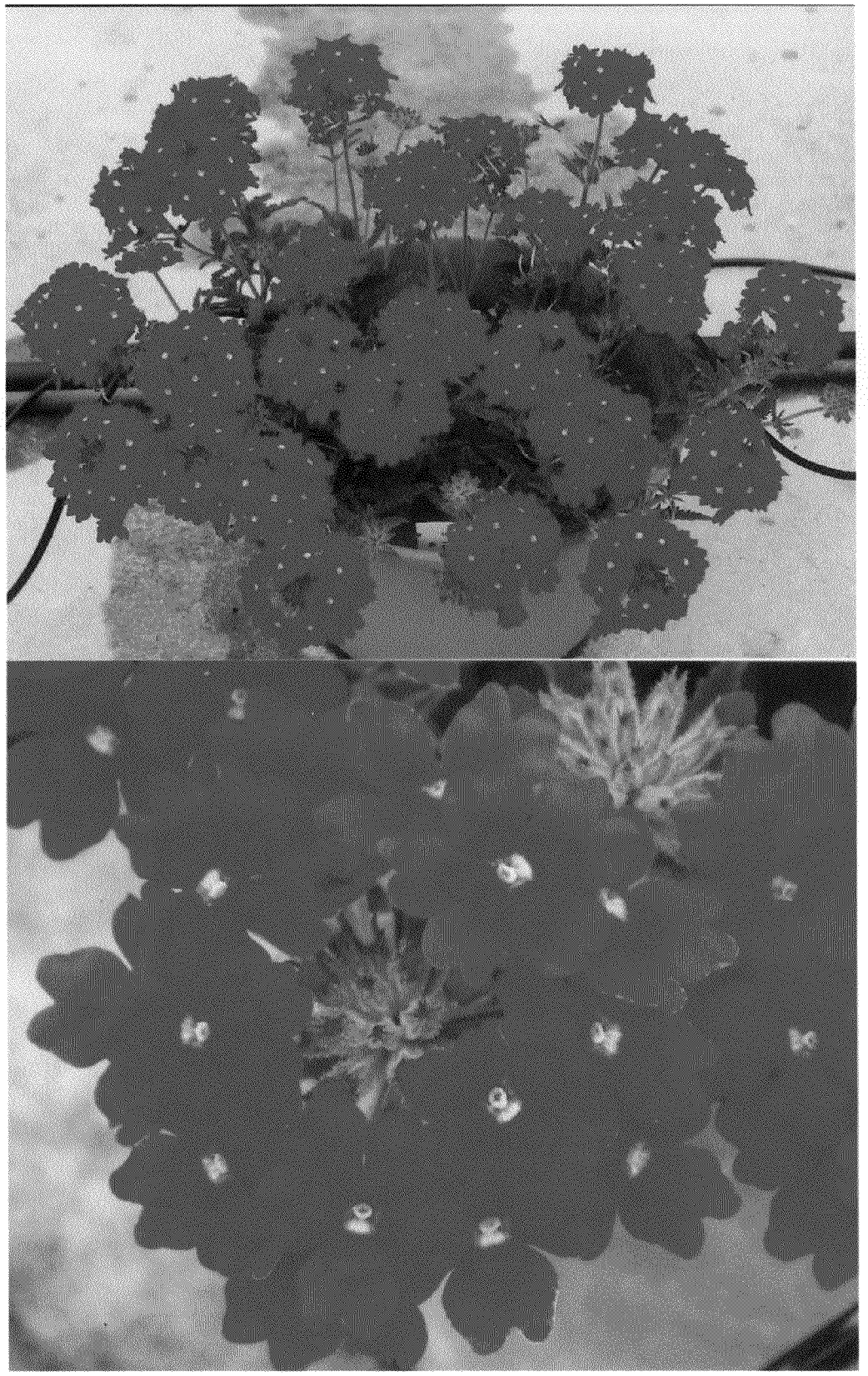

* * * * *